Figure 1:
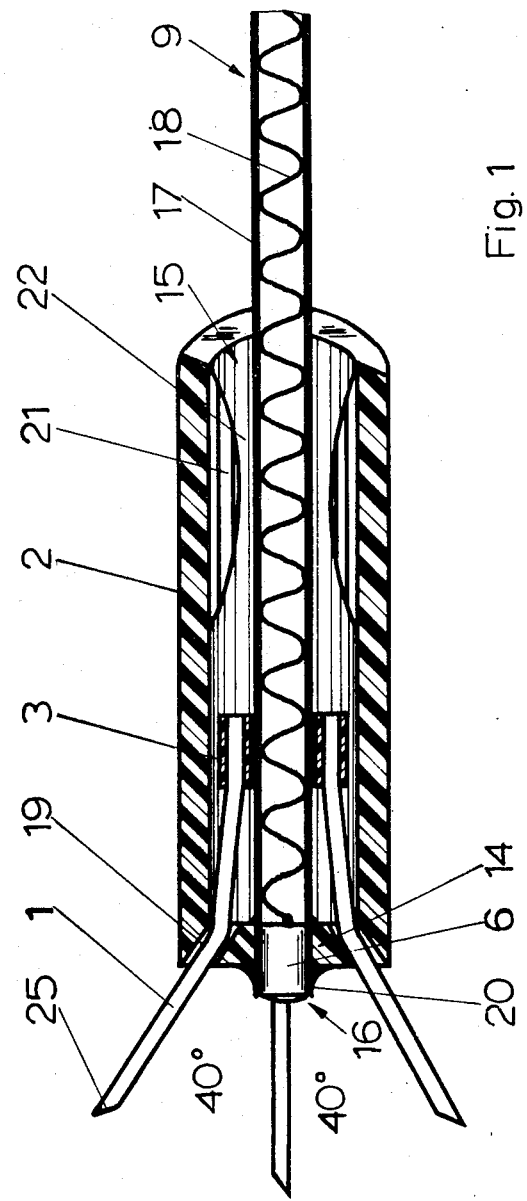

United States Patent [19]
Schmitt

[11] 3,976,082
[45] Aug. 24, 1976

[54] INTRACARDIAL STIMULATION ELECTRODE

[76] Inventor: German Schmitt, Ramertsweg 150/152, 4400 Munster, Germany

[22] Filed: Feb. 24, 1975

[21] Appl. No.: 552,716

[30] Foreign Application Priority Data
Feb. 25, 1974  Germany.................. 7406499[U]
July 9, 1974  Germany.................. 7423250[U]

[52] U.S. Cl. .................... 128/418; 128/419 P
[51] Int. Cl.² ............................ A61N 1/04
[58] Field of Search .......... 128/404, 418, 419 P, 128/419 PG, DIG. 4, 215, 218 M

[56] References Cited
UNITED STATES PATENTS

| | | | |
|---|---|---|---|
| 2,549,417 | 4/1951 | Brown | 128/218 M |
| 3,120,227 | 2/1964 | Hunter, Jr. et al. | 128/DIG. 4 |
| 3,719,190 | 3/1973 | Avery | 128/418 |
| 3,738,369 | 6/1973 | Adams et al. | 128/419 PG |
| 3,754,555 | 8/1973 | Schmitt | 128/418 |
| 3,814,104 | 6/1974 | Irnich et al. | 128/418 |
| 3,835,864 | 9/1974 | Rasor et al. | 128/419 P |

FOREIGN PATENTS OR APPLICATIONS
2,053,919  5/1972  Germany............... 128/419 P Primary Examiner—William E. Kamm
Attorney, Agent, or Firm—Cushman, Darby & Cushman

[57] ABSTRACT

An intracardial stimulation electrode for a heart pacemaker with a hollow insulating sleeve open at the rear, a metallic conductor head mounted at the front of the sleeve, a flexible hose attached in water tight relation to the head and extending through the sleeve, a wire conductor attached to the head and extending within the hose, a slide assembly mounted within the sleeve and about the hose for movement toward and away from the head to advance bristles which lock the electrode into heart tissue, out of and into the sleeve and structure at the rear of the sleeve for preventing withdrawal of the assembly.

7 Claims, 2 Drawing Figures

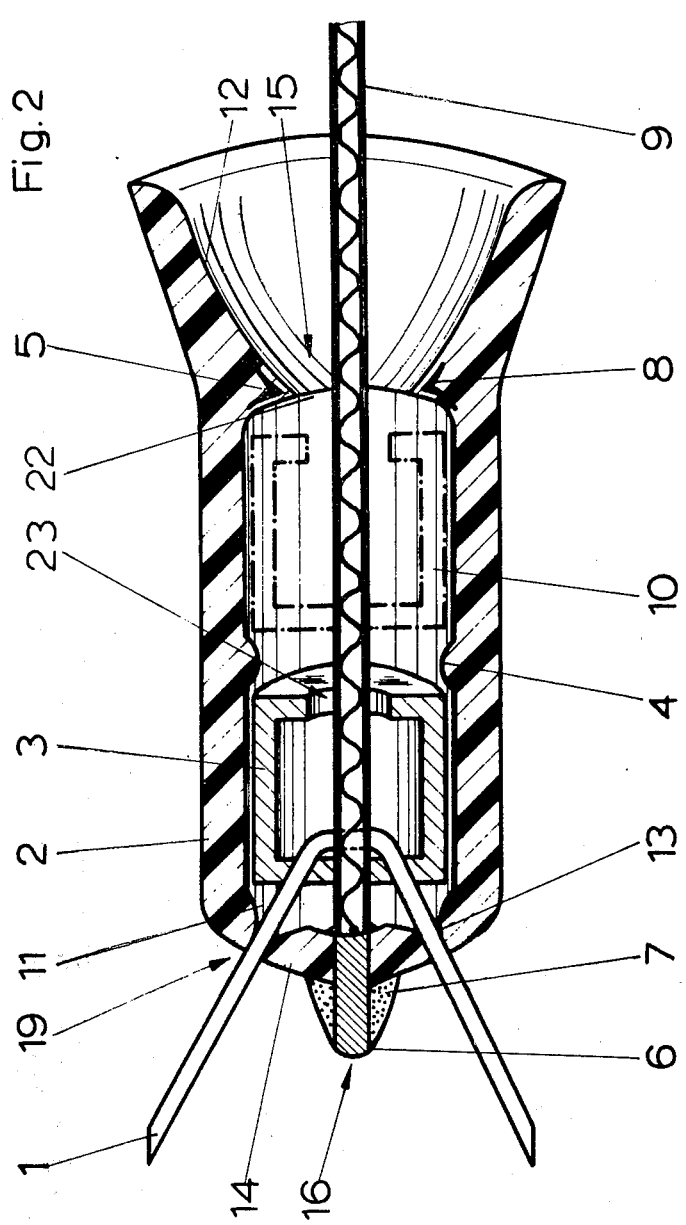

INTRACARDIAL STIMULATION ELECTRODE

The present invention relates to an intracardial stimulation electrode for heart pacemaker, wherein a conductor surrounded by an insulating sheath of shell is galvanically coupled (d-c coupled) to a metallic head contacting the wall of the heart muscle, whereby said metallic head is connected to a cylindrical sleeve of a non-conductive material, which sleeve has at its front end adjacent said metallic head, a plurality of resilient bristles adapted to be extended and retracted by means of a slide disposed within said sleeve, which bristles hook into the tissue of the heart muscle and thereby position said electrode.

Pacemaker electrodes of this type are inserted by means of a catheter through a vein, and are described in Res. Exp. Med. 161, pages 298 to 303.

In practice, however, the following problems arose in the handling of the known electrode:

When an error of placement is noted during the fastening or positioning of the electrode, the extended resilient bristles may be retracted by pulling a thread which is guided within the insulating sleeve of the conductor and which is connected to the slide. This operation must be performed prior to the withdrawing movement of the inserted catheter. It has been found that under the conditions of the surgical operation the above requirement is often neglected, such that the plastic bristles are extended during the movement of the catheter together with the electrode, thereby causing injury;

upon repeated extension and retraction, the tightness of the sealing between the bristles and the material of the head decreases such that body fluid may enter the interior of the electrode sleeve and cause short-circuiting therein. This results in high power consumption and in a weakening of the current density in the desired region of transition.

Accordingly, it is the object of the present invention to provide a stimulation electrode which avoids the abovementioned problems, which can be handled safely and easily, and which does not require any substantial changes when handled by persons who are familar with the manipulation of the known electrode.

This object is solved by an electrode of the type as outlined at the beginning, wherein said slide is adapted to be manipulated within said sleeve by means of an insertible and withdrawable, removable instrument, through a rear opening in said sleeve. Preferably, a catheter is suitable as the insertible and and retractible instrument, which is provided with a pair of relatively movable, concentric portions and one tip of which is adapted to be inserted into the interior of the sleeve and to be connected to the slide therein.

The novel arrangement renders possible to provide a relatively small punctiform metallic head in the axis of the sleeve. The bristles extend outward from the sleeve exteriorly of the metallic head and preferably form a square arrangement having point symmetry.

Furthermore, a flexure slack (non-rigid) conduit may be provided as the lead to the metallic head, because this conduit need not fulfill any mechanical function neither during insertion nor during removal of the stimulation electrode.

Inwardly protruding, reinforcing pads are provided interiorly of the sleeve, which pads define predetermined abutment points of the slide. In particular, it is proposed to render the slide to be adapted to be fixed in two positions, to enlarge the end of the sleeve in a funnel-shaped configuration, and to reinforce by an insert the narrowest point of the sleeve opening located within the mouth of the funnel. The latter measure has the effect that the slide is retained within the sleeve when it is being retracted so as to be prevented from slipping out from the sleeve.

Finally, it is proposed that the slide includes at least one aperture in its side opposing the rear opening of the sleeve, into which aperture an instrument passed through the sleeve opening may engage. These measures ensure absolutely safe manipulation of the electrode. In particular, it is thereby obtained that the resilient bristles are automatically retracted when the electrode connected to a catheter is withdrawn. It is only when the catheter is completely detached frm the electrode, that the bristles remain in their contemplated position.

Further advantages and properties of the invention are described below in connection with exemplary embodiments.

The invention is now further explained by referring to the drawings, wherein:

FIG. 1 shows a first embodiment of an electrode (according to the invention); and FIG. 2 shows a second embodiment of the invention.

FIG. 1 shows an electrode performing a similar function as the electrode mentioned as prior art at the beginning. Insertion of the electrode is performed with the aid of a guiding catheter which is inserted into a vein and advanced into the right hand ventricular cavity. Tests have shown that the electrodes, to be described in greater detail below, may be anchored to the muscles both of the heart cavity and of the auricle in such a manner that the electrodes are held in these positions without displacement or separation.

The electrode according to FIG. 1 comprises a cylindrical sleeve 2 made of a soft plastic material being compatible with the human body. The sleeve has a terminal wall 14 at its front end and an opening 15 in its rear end. The terminal wall 14 is penetrated by a platinum-iridium head 6 having an exposed contact face 16. The rear end of the head 6 merges into a plastic hose 17 which is connected to the plastic sleeve 2 in a completely water-tight manner. The hose 17 includes a metal wire 18 interiorly thereof, which wire serves to galvanically connect (d-c couple) the head 6 to a known power source. Hose and wire, in combination, form a flexible lead 9. The wire 18 within the hose 17 may be helically wound, braided or crotched-needled. In any case, it must have a certain longitudinal flexibility and bending flexibility. However, the lead does not fulfill any "mechanical" function, i.e. it is not used as a drawing or pushing element during placement of the electrode. Rather, tension and pressure forces are applied exclusively to the electrode by means of the guiding catheter.

A slide 3 is disposed within the sleeve 2, which slide is formed as a plastic cylinder and which supports the ends of four bristles 1 which are of elastic or resilient nature and which in their inactive condition assume approximately the shape as shown in FIG. 1. The bristles 1 are passed to the exterior through bores 19 provided in the terminal wall 14, and they terminate in bevelled tips 25. In the present embodiment, four bristles are provided which are arranged around the axis of the metallic head 6 with radial symmetry. The metallic head 6 per se is further protected by a toroidal insulator 20. The slide 3 is engaged by the tubular tip of the guiding catheter which is pushed over the conduit 9. The tip end (not shown) embraces the slide 3 such that the latter may be pushed to and fro within the sleeve together with the tip end. In order to prevent the slide 3 from being inadvertently withdrawn from the sleeve when the catheter is retracted, a reinforcing pad 21 is provided which is formed of plastic material and projects into the opening of the sleeve.

First, the electrode is intravenously inserted by means of a catheter into the intended position, with the bristles 1 of the electrode being retracted. Thereafter, the shell of the catheter is advanced to such extent that the bristles are projected from the sleeve and define an "anchoring" under an angle of about 40°. The bristles engage with the muscular tissue of the heart. When it is found by radiography or by test pulses that the correct position has not yet been reached, the outer shell of the guiding catheter is drawn back, whereby the slide 3 at the same time moves rearwardly within the sleeve so as to retract the extended bristles. In this condition, the electrode can then be placed into a different position without danger.

A sealing assembly can be omitted since the joint between the lead and the metallic head 6 is hermetically sealed, because control of the slide must no longer be effected from the interior of the lead as has been proposed in the prior devices.

Another advantage resides in the fact that this construction makes possible to insert an extremely small electrode head which provides reduction of weight on the one hand, and a higher current density in the contact region on the other hand. As a result of the lastmentioned advantage, the power consumption can be further reduced. Accordingly, the pacemaker battery will function over an extended period of time. Another important advantage is the fact that the electrode, owing to the novel construction, can be placed or attached so easily and safely that it may be implanted even into the auricle. Accordingly, the heart frequency may be adapted to the respective requirements, e.g. in the case of increased corporal stress. In the prior pacemaker electrodes, this possibility did not exist, such that these pacemaker operated constantly at the fixed frequency of about 70 throbs per minute. Tests performed with the hearts of dogs have shown that separation of the implanted electrode head did not occur even at a frequency of 120 throbs per minute.

FIG. 2 shown an embodiment of the electrode which is modified in some details thereof. The sleeve 2 is made of a plastic material, and it has a somewhat projectile-shaped configuration. The front terminal wall 14 is slightly bulged in forward direction. The bores 19 for the bristles 1 are of conical shape, as seen from the inner side of the sleeve, such that the bristles can be guided in positive manner.

The rear end of the sleeve and its opening 15 are formed as a funnel-shaped enlargement 12. The opening 15 has a restriction 22 the inner side of which is provided with a reinforcing insert 8. Another restriction is shown at 4. This latter restriction, although also projecting into the interior of the sleeve, has a smaller ramp effect.

In the illustrated embodiment, the slide 3 is formed as a cylindrical element having an opening 23 in its rear side. The bristles 1 are embedded into the slide, whereby — as shown in the FIG. — the bristles are substantially integral in pairs.

A portion of the guiding catheter extends into the opening 23. By means of this catheter, the slide 3 may be moved from a rear position 10 (shown in dashed lines) into a front position (shown in solid lines). Hereby, the restriction-pad 4 defines an abutment ramp or stop defining two fixed positions. The rear restriction 22 which, in addition, is reinforced or thickened, forms a "rigid" barrier which prevents the slide from slipping out of the opening 15.

The platinum-iridium head 6 is galvanically connected (d-c coupled) to a power source through a flexible lead 9 which is sealed to the sleeve body. A conical insulation 7 is arranged around the head, such that a contact surface 16 only is exposed.

This electrode is used and placed in a manner similar to that as described in connection with FIG. 1.

Silicone plastic material is particularly useful as a material for the sleeve of the electrode, while stainless steel (V2A) having a thickness of 0,5 millimeters is particularly suitable as the insert material for the reinforcing element 8.

What I claim is:

1. An intracardial stimulation electrode for a heart pacemaker comprising:
   a hollow insulating sleeve open at the rear,
   a metallic conductor head mounted at the end of said sleeve opposite the rear,
   a flexible hose attached to said head in water-tight relation at said one end and extending within said sleeve,
   an electrical conductor attached to said head and extending within said hose for coupling said head to a power supply,
   a plurality of bristles slidingly extending through said sleeve about said head for locking said electrode into heart tissue,
   a slide assembly disposed within said sleeve and about said hose for movement toward and away from said head, said assembly mounting said bristles for movement in and out of said sleeve as said assembly is moved by a catheter inserted in the rear of said sleeve to engage said slide assembly, and
   means adjacent the rear of said sleeve for preventing withdrawal of said assembly from said sleeve.

2. An electrode as in claim 1 wherein four said bristles are disposed in radial symmetry about the axis of said head.

3. An electrode as in claim 1 wherein said conductor is a non-rigid electrical wire.

4. An electrode as in claim 1 wherein said preventing means includes a reinforcing pad disposed within said sleeve adjacent the rear thereof constricting said sleeve to prevent withdrawal of said assembly.

5. An electrode as in claim 1 wherein said preventing means includes a narrowed portion of said sleeve adjacent the rear of said sleeve.

6. An electrode as in claim 5 wherein the rear of said sleeve has funnel-shaped enlargement.

7. An electrode as in claim 1 wherein said slide is provided with an aperture on the end facing said rear for receiving a catheter.

\* \* \* \* \*